US005667529A

United States Patent [19]

Butner

[11] Patent Number: 5,667,529

[45] Date of Patent: Sep. 16, 1997

[54] PATIENT CONTROLLED THERAPY TABLE

[76] Inventor: Tarry Adair Butner, 19 N. Ridge Rd., McHenry, Md. 21541

[21] Appl. No.: 395,904

[22] Filed: Feb. 28, 1995

[51] Int. Cl.$^6$ .................... A61F 5/00

[52] U.S. Cl. .................... 602/33; 5/617; 606/241

[58] Field of Search .................... 5/613, 614, 618, 5/620; 606/237, 241, 240, 245; 602/32, 33, 35–36

[56] References Cited

U.S. PATENT DOCUMENTS

| | | | |
|---|---|---|---|
| D. 249,360 | 9/1978 | Lacock | D24/3 |
| 951,515 | 3/1910 | Solsem | 606/241 |
| 1,171,713 | 2/1916 | Gilkerson . | |
| 1,205,649 | 11/1916 | Miller | 606/241 |
| 1,347,913 | 7/1920 | Rink | 602/32 |
| 1,399,034 | 12/1921 | Taplin | 606/238 |
| 2,494,746 | 1/1950 | Colston . | |
| 2,579,783 | 12/1951 | Branto . | |
| 3,132,897 | 5/1964 | Linden | 5/618 |
| 3,311,933 | 4/1967 | Peterson | 5/614 |
| 3,868,103 | 2/1975 | Pageot et al. | 5/618 |
| 4,059,255 | 11/1977 | Perold . | |
| 4,546,766 | 10/1985 | Hill et al. . | |
| 4,582,311 | 4/1986 | Steffensmeier | 5/622 |
| 4,710,991 | 12/1987 | Wilmore et al. | 5/635 |
| 4,943,041 | 7/1990 | Romein | 5/620 |
| 4,961,236 | 10/1990 | Luconi . | |
| 5,158,568 | 10/1992 | Riddle et al. | 5/618 |
| 5,468,216 | 11/1995 | Johnson et al. | 5/618 |

OTHER PUBLICATIONS

Hallmed Inc., Hill Laboratories "The Rath Mechanical Treatment Table", Carnegie, PA, 1993.

PCI, "The Doctor's Prescription Fro Enhanced Spine Rehabilitation", Austin Texas, Oct., 1994.

Repex Corporation of New Zealand, "The Original McKenzie Repex", Howard Wright Ltd. Manufacturer, 1994.

*Primary Examiner*—Michael Buiz
*Assistant Examiner*—Nancy Mulcare
*Attorney, Agent, or Firm*—Mary Louise Walcek

[57] ABSTRACT

The invention is a physical therapy table having moveable sections allowing the patient to be placed in different physical positions as part of an individual physical therapy regimen wherein the patient himself applies and controls extension, traction and mobilization therapy.

19 Claims, 3 Drawing Sheets

PATIENT CONTROLLED THERAPY TABLE

The invention is a physical therapy table having moveable sections allowing the patient to be placed in different physical positions as part of an individual physical therapy regimen. Through the use of manually operated means, the patient, supported on the top surface of the table, moves various sections of the table without the assistance of an attending therapist.

The Lorang patent U.S. Pat. No. 2,851,320 discloses a chiropractic table provided with hydraulic means allowing the entire table top surface to be moved up, down or tilted at a desired angle by the therapist (see col. 1, line 33–38). Sections of the table cannot be moved independent of one another and the patient cannot operate the moving means while positioned on the table surface.

The operation of the Table in the H. C. Perold U.S. Pat. No. 4,059,255 is similar to that of Lorang above in that hydraulic means are used to raise, lower or tilt the table surface. These movements cannot be made by the patient.

U.S. Pat. No. 1,171,713 to J. K. Gilkerson discloses a sectional treatment table wherein the head and foot portions of the table may be inclined toward or away from each other as desired. This allows the patient to be positioned with head and feet lower or higher than the midsection of the body (FIGS. 5 and 6). The movement of the portions of the table cannot be performed by the patient while on the table and the assistance of an attendant is required.

The device described in the L. S. Luconi patent, U.S. Pat. No. 4,961,236, is hydraulically operated to raise and then lower the head portion of a bed mattress. This device is electrically operated through computer means (see col. 1, lines 65–68; col. 2, lines 1–6 and col. 3, lines 53–68).

The Hill et al. patent, U.S. Pat. No. 4,546,766, relates to a traction appliance associated with a treatment table (see Abstract). This appliance cannot be operated by the patient on the table.

U.S. Pat. No. 4,582,311 to L. A. Steffensmeier discloses a hydraulically controlled chiropractic table for variable tension flexing. The pelvic section of the table can be tilted independently from the upper body section, but requires an attendant to operate the mechanism (see col. 1, lines 48–52).

The patent to A. L. Colston, U.S. Pat. No. 2,494,746, describes a motor operated treatment table able to rotate a section of the table surface. The movement cannot be controlled by the patient (see FIGS. 1 and 2).

U.S. Pat. No. 2,579,783 to A. F. Branto discloses a two piece head rest (21) and an chin notch (19*a*) used in conjunction with a folding treatment table (see FIG. 1).

Another two piece headrest is described in U.S. Pat. No. 4,710,991 to Wilmore et al. (see Abstract).

Product information relating to the Rath Mechanical Treatment Table produced by Hill Laboratories Companies shows a treatment table specifically designed for practicing the Mckenzie technique. The angular movement of the upper body portion of the table surface may be electrically controlled by the patient while on the table surface. An elongated hole is provided in the upper portion for facial support. However, the overall shape of the upper portion does not allow the patient to operate a mechanically actuated hydraulic lifting jack.

Product information relating to the REPEX discloses a table with a two section treatment surface. The two sections can be tiled inwardly or outwardly to practice the McKenzie technique. Movement of the table sections is controlled by the therapist through a remote hand piece. The shape and size of the facial and shoulder supports do not permit operation by the patient.

Product information from PCI (Physicians Consulting Incorporated) shows a treatment table wherein the head and foot portions of the table may be tilted away from or towards each other as desired. The tilting motion is continuous and is patient controlled through computer means.

OBJECTS OF THE INVENTION

A first object of the invention is a physical therapy treatment table having a two section treatment surface wherein the angular movement of each section is independently, manually and mechanically controlled by the patient resting on the treatment surface.

An object of the invention is a physical therapy treatment table provided with a generally U-shaped facial and shoulder support allowing free movement of the patient's arms to control the angular movement.

Another object of the invention is a physical therapy treatment table provided with means to apply traction to the patient, which means is patient controlled.

Still another object of the invention is a physical therapy treatment table provided with means to apply a mobilization pressure to the patient which means is also patient controlled.

Another object of the invention is a physical therapy treatment table provided with a mobilization bar constructed in such a fashion that pressure is not applied to the spine itself but to the musculature adjacent the involved spinal segment.

Still another object of the invention is a physical therapy table with means to prevent a patient from slipping off the table during extension of the body.

BACKGROUND OF THE INVENTION

The physical therapy table of the invention has been designed for use with the McKenzie technique, a passive exercise for treatment of spinal problems, but may be used for many other physical therapy purposes such as massage, stretching and muscle-energy techniques.

The spinal column is made of vertebrae and discs. Movement of the spine takes place at the disc, which is a soft deformable tissue. The disc is shaped like a jelly doughnut wherein the jelly center is the nucleus and the dough portion is a thick fibrous wall called the annulus. When a person bends forward (flexion), the anterior or front part of the disc is compressed, the posterior or back part of the disc expands and the nucleus is pushed posteriorly against the annulus. The opposite happens with a backward bend (extension): the posterior part of the disc is compressed, the anterior part expands and the nucleus moves anteriorly. The same type of disc deformation with nucleus movement also happens in side bending. In a normal disc, the nucleus returns to it's central position when the spine returns to a neutral resting posture.

With flexion of the lumbar spine and the associated compression of the anterior nucleus, the pressure within the disc increases dramatically and this increased pressure is directed against the posterior wall. Many people maintain a flexed sitting posture in the lumbar region for sustained periods every day. They sleep in a flexed posture, sit or bend over to dress, sit to drive a car to work and sit at work and at meals. At the end of the day, they sit in a recliner to relax. Most daily routines require a great deal of flexion but almost no extension to counter the effects of this flexion.

When the flexed posture is maintained for most of the time, the nucleus accumulates on the back wall of the disc.

Months and years of flexion without extension causes the anterior annulus to shorten. Extension becomes uncomfortable and the full extension range of motion is lost. This is called extension dysfunction.

With prolonged or repeated flexion, the posterior annulus becomes over stretched and weakened and, with continued high pressure from the nucleus, it begins to bulge. As it bulges (deforms) low back pain is felt. At some point in the process, the pressure from the nucleus is sufficient to begin breaking through the inner layers of the posterior annulus. By the time this fissuring has broken through to the middle layers of the annulus, the patient is reporting constant and severe low back pain. This mechanical deformation of the disc which remains when we return to a normal resting position and the possible annulus damage is called posterior disc derangement.

SUMMARY OF THE INVENTION

According to the invention, a patient suffering from a posterior disc derangement, for example, is placed face down on the table and the upper body section is rotated upward toward the lower body section so as to bend the patient backwards urging the disc back into alignment. Therapy begins with a slight angle and gradually increases to a more acute angle. Movement towards a more acute angle is determined by symptoms felt by the patient. The patient can adjust the angle by using a hand operated hydraulic jack located under upper body portion.

While on the table, traction may be applied to the patient's body in all positions of extension using a two piece body harness. The top section holds the patient's upper body stationary on the table. The bottom section of the harness is joined to tightening means by a cable extending under the table. The tightening means is preferably a winch but may be any type of cable shortening or tightening device. The tightening means is located under the table and is operated by the patient to apply a variable amount of tension to the cable and thus to the lower harness. The top section of the harness may also be connected to a second tightening means allowing the patient to apply traction to the upper body.

Back extension may be enhanced through a mobilization bar applied to the involved segment of the back. The amount of pressure applied by the mobilization bar is also patient controlled by means located under the table.

This treatment table allows the patient to apply the above procedures to himself and to take an active role in his treatment. Because the patient is the one who will feel the pain while slowly applying traction, extension and mobilization, the patient will be less likely than the therapist to apply these procedures too aggressively, thus enhancing treatment safety.

Because the patient controls the movement of the upper body section, the amount of tension for traction and the amount of pressure applied by the mobilization bar, his arms must be free to use all the control devices. The head and shoulder support has a generally U-shape whose width is less than the width of the remainder of the table surface. This provides support for the shoulders and head, allows the patient's arms to move freely, enables the patient to breath easily and to see the control devices.

A padded mobilization bar applies pressure to the involved segment of the back. However, the padding is not continuous over the length of the bar. The section of the bar lying over the spine or the spinal process has no padding and the section lying over the adjacent spinal muscles is thickly padded so that the mobilization pressure is applied to the musculature adjacent the involved spinal segment and not directly to the spine.

DETAILED DESCRIPTION OF THE DRAWINGS

Figure 1:
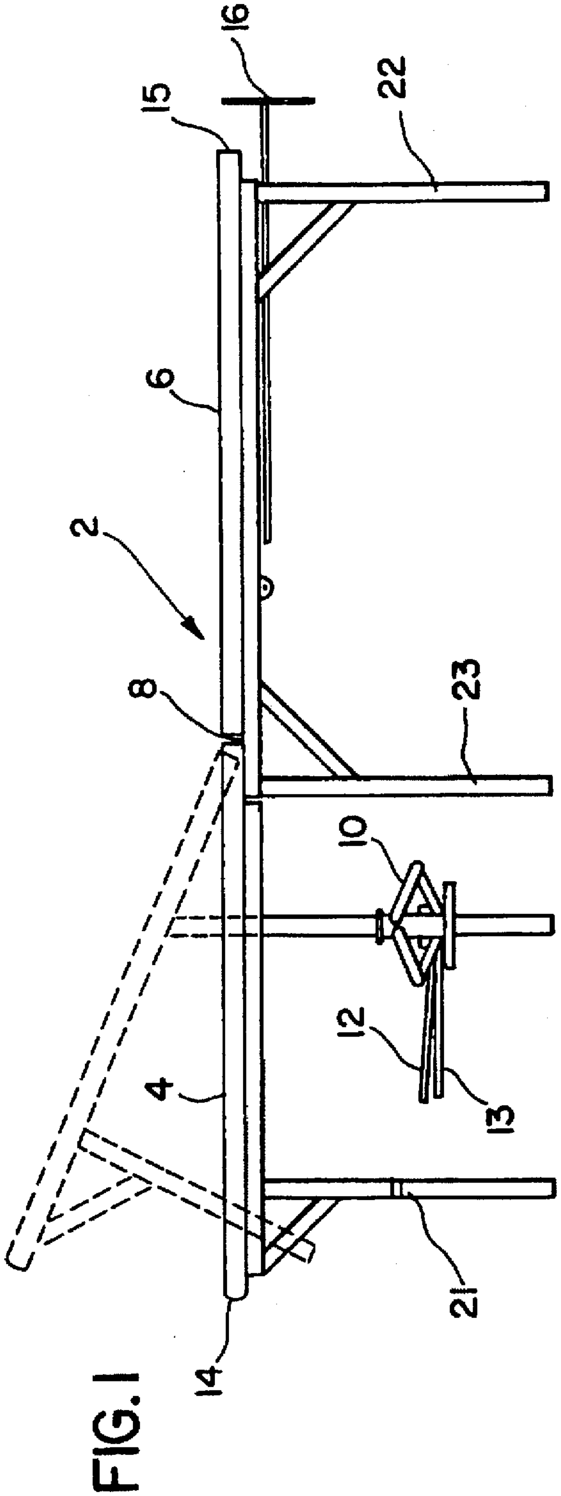
FIG. 1 is a side view of the table of the invention with the extended position shown in dotted line.

The invention will be described referring to FIG. 1, a side view of the treatment table wherein the patient treatment surface is generally indicated by 2. Surface 2 has two sections, an upper body section generally indicated at 4 and a lower body section generally indicated at 6 rotatingly connected at the center of rotation 8. A hydraulic jack, 10 located under upper body section 4 operated by the patient using jack handle 12, is used to raise head end 14 and to thus rotate upper body section 4 upwardly toward lower body section 6. The raised position is shown in dash lines. An extendible foot plate 16 is provided at foot end 15 to keep the patient from slipping toward the foot end when upper body section 4 is in the raised or extended position. The upper body section 4 is lowered by releasing jack release 13. The treatment surface is supported by a pair of upper body legs 21, a pair of lower body legs 22 and a pair of central legs 23.

Although this embodiment uses a hydraulic jack, other lifting means such as an electric motor, a mechanical jack or any other pump or jack means may be used.

Not shown is another mechanism whereby when the patient rotates upper body section 4 upwardly, lower body section 6 is simultaneously rotated upwardly toward upper body section 4, both sections rotating about center of rotation 8. This mechanism comprises a cable and pulley system whereby the part of the lifting force of jack 10 is translated to a lever arm means raising lower body section 6.

Figure 2:
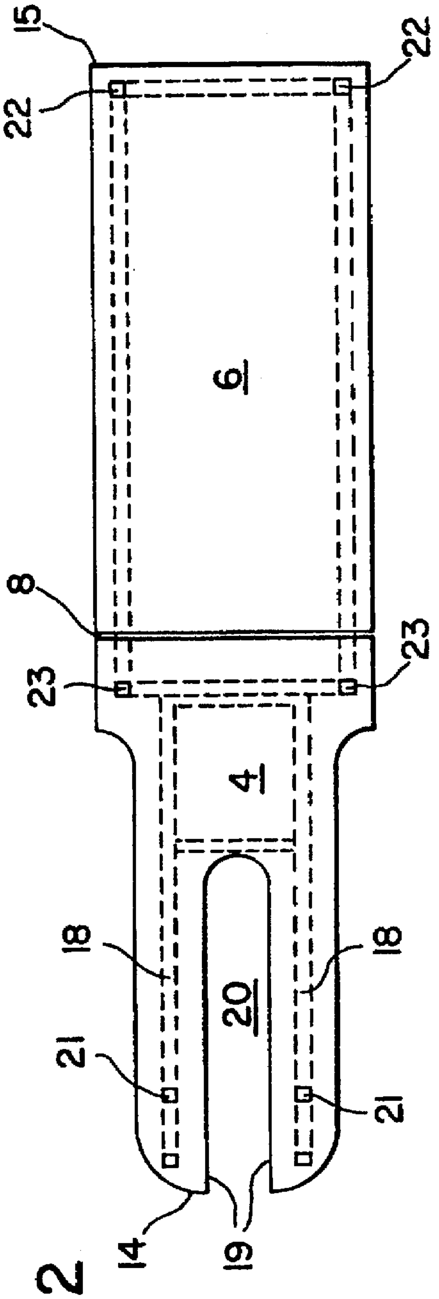
FIG. 2 is a view from above of FIG. 1.

FIG. 2, a view from above of FIG. 1, shows the structure of head end 14. The dashed line shows the frame and support members and the small squares indicate the upper ends 14 of legs 21, 22 and 23. The end of upper body section 4 has a general U-shape formed by arms 18 and slot 20.

During treatment, the patient rests face down on surface 2 of FIG. 1 with his shoulders resting on arms 18 and his face in slot 20. Since slot 20 is more narrow than his head is wide, his head is supported by the inner edges 19 of arms 18. This enables the patient to breath easily and to see the control devices. The width of head end 14 is more narrow than his shoulders which allows his arms to move freely to operate the control devices, for example, hydraulic jack 10 and mobilization handles 46 described below.

Figure 3:
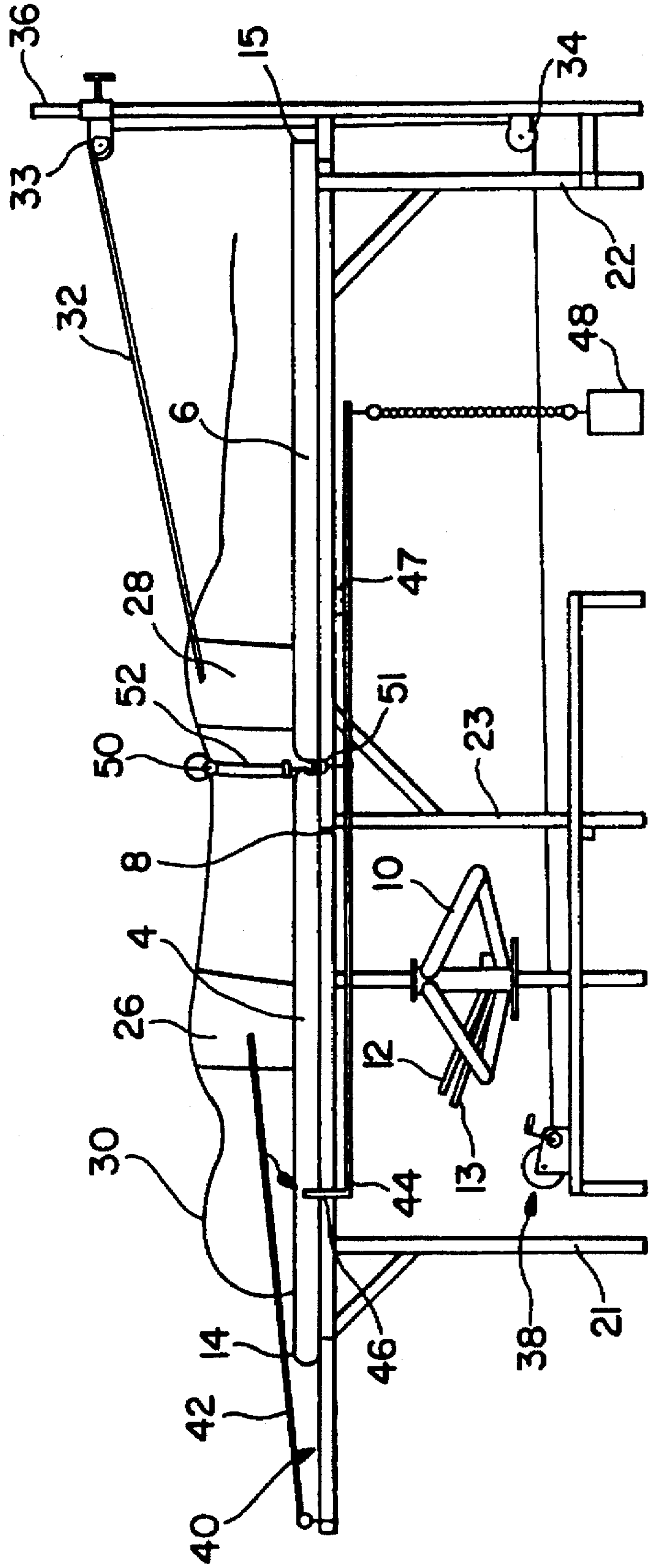
FIG. 3 is a side view of the table of the invention provided with the mobilization bar and the traction means.

FIG. 3 is a side view of the treatment table showing the traction means and the mobilization means. The patient 30 is placed face down on treatment surface 2 comprising upper body section 4 and lower body section 6. Upper body harness 26 is fixed around the upper torso of patient 30 and lower body harness 28 is fixed around the hips. Traction line 32 is attached to lower harness 28, goes around upper pulley 33 and lower pulley 34 located on pulley support 36 and is connected to the traction control device, in this case a patient operated winch 38 located under upper body section 4. Line 42 connects upper body harness 26 to upper harness base 40 and is adjusted to keep patient 30 from sliding toward foot end 15 when traction is applied. In this embodiment, there is no foot plate. Also, there is no connection between upper harness 26 and lower harness 28 except for the body of patient 30. To apply traction, patient 30 operates winch 38 to tighten traction line 32. This pulls his lower body away from his upper body, elongates the spine and separates the vertebrae allowing a bulging disc to return to its proper alignment in the spinal column.

In another embodiment not shown, a second traction winch, also located under upper body section 4, is connected to upper body line 42. This allows the patient to apply traction to the upper body. Thus, traction may be applied to the upper body, to the lower body or to both depending on therapeutic need and/or patient comfort. Moreover, the upper body harness may be removed and a cervical harness (not shown) attached to the head of the patient allowing cervical traction to be used.

The mobilization means is also shown in FIG. 3. This mobilization means comprises mobilization bar 50, and lever arm 44 connected to mobilization bar 50 at connection point 51 by way of flexible connecting means 52. Since this is a side view of the treatment table, only one side of the mobilization means is shown. However a second side, a mirror image of the one shown, is located one the other side of the table, parallel to the one shown. See FIG. 4 for another view of the mobilization means.

In mobilization treatment, a padded mobilization bar 50 is applied across the back of the patient to the involved segment of the spine. Bar 50 is connected to mobilization lever arm 44 at connection point 51 by way of flexible connecting means 52. Although the drawing shows only one connection point 51, several may be provided to allow the location of the mobilization bar to be moved to the particular segment of the spine needing treatment. In fact, connection point 51 may be a bar for sliding attachment of the flexible connecting means allowing the bar location to be fine tuned. The remainder of the mobilization means is located below treatment surface 2 and is operated and controlled by the patient.

Lever arm 44 is provided with handle 46 and rotates about lever arm center of rotation 47 located on the table framework located below treatment surface 2. A counter balance 48 is provided on lever 44 at the end opposite handle 46. To apply mobilization pressure, patient 30 presses downward on handle(s) 46 of lever(s) 44 pulling flexible connecting means 52 and mobilization bar 50 downward. This applies pressure through bar 50 to the involved segment of the back.

Figure 4:
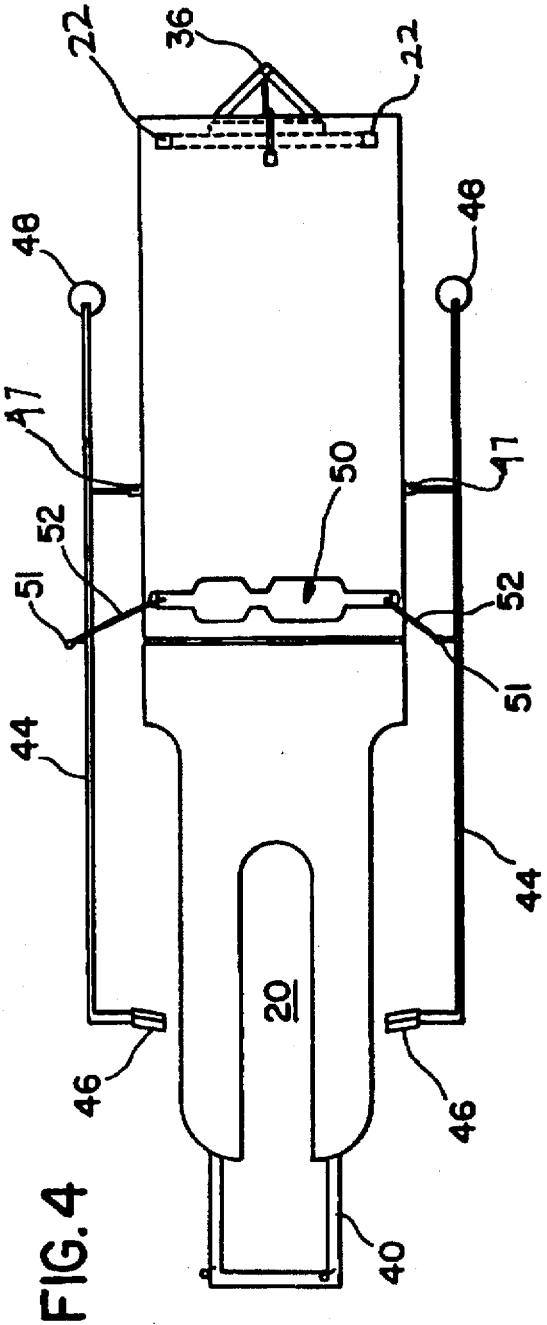
FIG. 4 is a view from above of FIG. 3.

FIG. 4 is a view from above of FIG. 3 and shows both sides of the mobilization means. Each side comprises lever arm 44 provided on the head end with handle 46 and on foot end with counter balance weight 46. Lever arm rotates about the center of rotation 47. The mobilization bar 50 is connected to lever 44 at point 51 by means of flexible connector 52.

Figure 5:
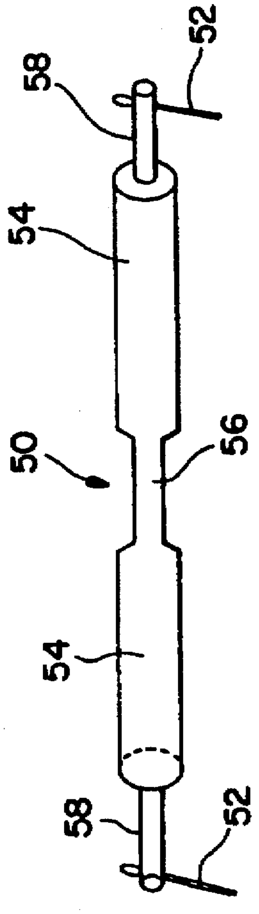
FIG. 5 shows the mobilization bar with details of the padding.

FIG. 5 shows details of the mobilization bar generally indicated at 50. Padded portions 54 of the bar are applied to the musculature at the sides of the spine. Note that bar 50 is provided with a central narrow portion or notch 56. When mobilization bar 50 is laid across the spinal column, notch 56 is placed directly over the spine so that the mobilization pressure will not be directly applied to the bones but to the surrounding musculature. By moving handles 46 up and down, the patient may move mobilization bar 50 to massage this musculature. The pressure of the mobilization bar may be bilateral or unilateral. It may also be greater on one side than on the other.

The main benefit provided by the present invention is that it is controlled and operated by the patient. While resting on the table surface, the patient is able to extend his back by operating the means rotating head end 14 upwardly. The patient can also apply traction to the body by operating winch 38 attached to harnesses 26 and 28. The patient can even apply mobilization pressure and massage to the affected portion of the spine by manipulating handle 46 to move mobilization bar 50 as desired.

Although it is advantageous for all three features, namely, extension, traction and mobilization to be on the same treatment table, it is not necessary for all three to be provided. The invention described is not intended to be limited to the embodiments disclosed but includes modifications made within the true spirit and scope of the invention.

I claim:

1. I claim a patient operated treatment table comprising:

a treatment surface having two sides and an upper body section with a head end and a first connecting end and a lower body section with a second connecting end and a foot end wherein the first connecting end of the upper body section and the second connecting end of the lower body section are mutually rotatingly connected; and patient manually operated mechanical means for rotating the head end of the upper body section upwardly toward the lower body section; wherein:

the head end of the upper body portion is a U-shape surface with a base and arms, and the base of the U-shape is adapted to support a patient's chest, and the arms of the U-shape are adapted to support a patient's shoulders and head, and the width of the surface of the U-shaped head end is more narrow than the width of the lower body portion.

2. I claim a table according to claim 1, including patient manually operated mechanical means for applying traction to the patient wherein the means applying traction comprises:

an upper body harness adapted to be fixed about a patient's upper torso when the patient is resting face down on the treatment surface with head, chest and shoulders resting on the U-shaped head end, said harness capable of securing the upper torso to the upper body section of the treatment surface, and a lower body harness adapted to be fixed about the patient's lower torso and provided with a cable extending to the foot end of the lower body section, beneath the surface and then to a cable tightening means located beneath the U-shaped head end within reach of the patient.

3. I claim a table according to claim 1, including patient manually operated mechanical means for applying mobilization pressure to the patient wherein the means applying mobilization pressure comprises:

a mobilization bar with two ends, said bar positioned to extend across the back of a patient resting face down on the treatment surface with head, chest and shoulders resting on the U-shaped head end; and levers extending along the two sides of the treatment table and extending from the upper body section to the lower body section, each adapted to be rotated about a center of rotation located on the respective side of the treatment surface, each lever is connected to one of the two ends of the mobilization bar, each lever being provided with a handle toward the head end and within reach of the patient and a counter balance weight toward the foot end of the treatment table;

wherein downward pressure on the handles causes the mobilization bar to contact and press downwardly on the patient's back.

4. I claim a table according to claim 1, wherein the mechanical means rotating the upper body section is a hydraulic jack located under the upper body section and is adapted for operation by a patient resting face down on the treatment surface with head, chest and shoulders supported by the U-shaped head end, said hydraulic jack capable of raising the head end of the upper body section to rotate the upper body section toward the lower body section.

5. I claim a table according to claim 1, including a second patient manually operated mechanical means for rotating the foot end of the lower body section upwardly and toward the upper body section.

6. I claim a table according to claim 5, wherein the mechanical means for rotating the lower body section is a hydraulic jack located under the lower body section, said jack adapted for operation by a patient resting face down on the treatment surface with head, chest and shoulders supported by the U-shaped head end, said hydraulic jack capable of raising the foot end of the lower body section to rotate the lower body section toward the upper body section.

7. I claim a table according to claim 4, wherein said patient operated mechanical means is adapted to simultaneously rotate the head end of the upper body section upwardly and toward the lower body section and the foot end of the lower body section upwardly and toward the upper body section.

8. I claim a patient operated treatment table comprising:

a treatment surface having two sides, an upper body section with a head end and a first connecting end and a lower body section with a second connecting end and a foot end wherein the first connecting end of the upper body section and the second connecting end of the lower body section are mutually rotatingly connected; and patient manually operated mechanical means for rotating the upper body section toward the lower body section; and patient operated mechanical means for applying traction to the patient comprising:

an upper body harness adapted to be fixed about a patient's upper body when the patient is resting face down on the treatment surface, said harness provided with a first cable extending to the head end, then extending beneath the treatment surface and then to first cable tightening means located under the head end within reach of the patient; and a lower body harness adapted to be fixed about the patient's lower body and provided with a second cable extending to the foot end of the lower body section then extending beneath the treatment surface and then to a second cable tightening means located under the head end and within reach of the patient.

9. I claim a table according to claim 8, wherein:

the head end of the upper body section is a U-shape with a base, arms and surface, the base of the U-shaped head end is adapted to support a patient's chest and the arms of the U-shaped head end are adapted to support a patient's shoulders and head, and the width of the surface of the U-shaped head end is more narrow than the width of the lower body section.

10. I claim a table according to claim 8, including patient manually operated mechanical means applying mobilization pressure to the patient and comprising:

a mobilization bar with two ends, said bar positioned to extend across the back of a patient resting face down on the treatment surface; and levers extending along each of the two sides of the treatment table and extending from the upper body section to the lower body section, each adapted to be rotated about a center of rotation located on the respective side of the treatment surface, each of said levers connected to one of two ends of the mobilization bar, each lever being provided with a handle toward the head end of the upper body section and within reach of the patient, and a counter balance weight toward the foot end of the treatment table;

wherein downward pressure on the handles causes the mobilization bar to contact and press downwardly on the patient's back.

11. I claim a table according to claim 8, wherein the mechanical means rotating the upper body section is a hydraulic jack located under the upper body section and is adapted for operation by the patient resting face down on the treatment surface, said hydraulic jack capable of raising the head end of the upper body section to rotate the upper body section toward the lower body section.

12. I claim a table according to claim 8, including patient manually operated mechanical means for rotating the foot end of the lower body section upwardly and toward the upper body section.

13. I claim a table according to claim 12, wherein the mechanical means rotating the lower body section is a hydraulic jack adapted for operation by the patient resting face down on the treatment surface, said hydraulic jack capable of raising the foot end of the lower body section so as to rotate the lower body section toward the upper body section.

14. I claim a patient operated treatment table comprising:

a treatment surface having two sides and an upper body section and a lower body section, said surface adapted to support a patient receiving treatment;

patient operated mechanical means for applying mobilization pressure to the patient, wherein the mechanical means comprises:

a mobilization bar with two ends, said bar positioned to extend across the back and spine of a patient resting face down on the treatment surface;

levers extending along the two sides of the treatment surface and extending from the upper body section to the lower body section, each lever adapted to rotate about a center of rotation located on the respective side of the treatment surface, each of said levers connected to one of the two ends of the mobilization bar, each lever being provided with a handle toward the head end of the upper body section within reach of the patient, and a counter balance weight toward the foot end of the of the treatment table;

wherein downward pressure on the handles causes the mobilization bar to contact and press downwardly on the patient's back.

15. I claim a table according to claim 14, wherein the mobilization bar is padded and further wherein the padded bar is provided at its center with an unpadded annular notch, said notch adapted to fit over the spine of a patient lying on the treatment surface.

16. I claim a table according to claim 14, wherein the upper body section has a head end and a first connecting end and the lower body section has a second connecting end and a foot end and further wherein the first connecting end of the upper body section and the second connecting end of the lower body section are mutually rotatingly connected.

17. I claim a table according to claim 14, wherein:

the head end of the upper body section is a U-shape with a base, arms and a surface, and the base of the U-shape is adapted to support a patient's chest, and the arms of the U-shape are adapted to support a patient's shoulders and head, and the width of the surface of the U-shaped head end of the upper body section is more narrow than the width of the lower body section.

18. I claim a table according to claim 14 including patient manually operated mechanical means adapted to rotate the head end of the upper body section upwardly toward the lower body section and patient manually operated mechanical means to rotate the foot end of the lower body section upwardly toward the upper body section.

19. I claim a table according to claim 16, including patient manually operated mechanical means for applying traction to the patient wherein said means comprises:

an upper body harness adapted to be fixed about a patient's upper torso when the patient is resting face down on the treatment surface, said harness securing the upper torso to the upper body section of the treatment surface, and a lower body harness adapted to be fixed about the patient's lower torso and provided with a cable extending to the foot end of the lower body section, beneath the treatment surface and then to a cable tightening means located beneath the U-shaped head end within reach of the patient.

* * * * *